United States Patent [19]
Karasawa et al.

[11] Patent Number: 5,268,506
[45] Date of Patent: Dec. 7, 1993

[54] PROCESS FOR PRODUCING α, β-UNSATURATED CARBOXYLIC ACID

[75] Inventors: Minato Karasawa, Mobara; Takeshi Hiraiwa; Sinji Tokunoh; Hiroharu Kageyama; Kanemitsu Miyama; Masamitsu Inomata, all of Mobara, Japan

[73] Assignee: Mitsui Toatsu Chemicals, Incorporated, Tokyo, Japan

[21] Appl. No.: 34,464

[22] Filed: Mar. 19, 1993

[30] Foreign Application Priority Data

Mar. 27, 1992 [JP] Japan .................. 4-070871

[51] Int. Cl.$^5$ ............... C07C 51/353; C07C 57/04
[52] U.S. Cl. .................. 562/599; 562/400; 562/405; 562/495; 562/503
[58] Field of Search ............ 562/599, 400, 405, 495, 562/503; 560/212

[56] References Cited

U.S. PATENT DOCUMENTS

| | | | |
|---|---|---|---|
| 4,464,539 | 8/1984 | Hashimoto et al. | 560/212 |
| 4,990,662 | 2/1991 | Hagen et al. | 562/599 |
| 5,068,399 | 11/1991 | Naito et al. | 562/599 X |
| 5,102,849 | 4/1992 | Kemp et al. | 502/214 |

FOREIGN PATENT DOCUMENTS 181718 5/1986 European Pat. Off. .

Primary Examiner—Arthur C. Prescott
Attorney, Agent, or Firm—Burns, Doane, Swecker & Mathis

[57] ABSTRACT

An α, β-unsaturated carboxylic acid is produced by catalytically reacting an α-hydroxycarboxylic acid amide of the formula (1),

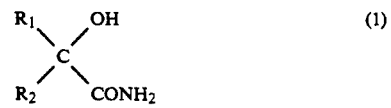

where $R_1$ and $R_2$ are independently selected from the group consisting of hydrogen and $C_1$-$C_4$ alkyl groups, provided that at least one of $R_1$ and $R_2$ is the alkyl group, with water in the presence of a solid acid catalyst containing a high surface area rare earth phosphate anhydride having the monoclinic system structure producible by heating a rare earth phosphate of the hexagonal system structure at 60°–200° C. in a solution of an inorganic acid, an inorganic acid salt and/or an inorganic acid ester where the molar ratio of the inorganic acid component to the rare earth phosphate of the hexagonal system structure is 0.5–400.

22 Claims, 1 Drawing Sheet

PROCESS FOR PRODUCING α, β-UNSATURATED CARBOXYLIC ACID

BACKGROUND OF THE INVENTION

1. Field of the Invention

The present invention relates to a process for producing an α, β-unsaturated carboxylic acid, and more particularly, to a process for producing an α, β-unsaturated carboxylic acid in the presence of an improved solid acid catalyst.

α, β-Unsaturated carboxylic acids are used as starting materials for preparing α, β-unsaturated carboxylic acid esters. Among them, methacrylic acid is a starting material for producing methyl methacrylate from which poly(methyl methacrylate) exhibiting high weatherability and transparency can be prepared, and therefore, is very useful in industry.

2. Description of the Related Art

Heretofore, there are known processes for producing α, β-unsaturated carboxylic acids, for example, Japanese Patent Publication No. Sho 63-10940 (U.S. Pat. No. 4,464,539) discloses a method for producing an α, β-unsaturated carboxylic acid which comprises bringing water and an α-hydroxycarboxylic acid amide prepared by hydration of cyanohydrin into contact with a solid acid catalyst. In this case, as a representative solid acid catalyst, there may be used a catalyst containing a phosphoric acid salt such as lanthanum phosphate, cerium phosphate and the like.

As a result, for example, by using a rare earth metal phosphate of a hexagonal system structure produced by a conventional method as a solid acid catalyst, there can be obtained methacrylic acid in a 75-85 mole % yield from a 4.8 mole % aqeous solution of α-hydroxyisobutyramide at a liquid hourly space velocity (LHSV) of 0.2-1.3 hr$^{-1}$ and at a reaction temperature of 300°-400° C.

However, in an industrial production, the α, β-unsaturated carboxylic acid obtained by the above-mentioned method is continuously used as a starting material for an α, β-unsaturated carboxylic acid ester, and therefore, there has been demanded a solid acid catalyst capable of keeping a high catalytic activity at a lower reaction temperature for a long period of time under a higher catalytic load.

SUMMARY OF THE INVENTION

An object of the present invention is to provide a process for producing an α, β-unsaturated carboxylic acid in good yield from an α-hydroxycarboxylic acid amide.

According to the present invention, there is provided a process for producing an α, β-unsaturated carboxylic acid which comprises catalytically reacting an α-hydroxycarboxylic acid amide of the formula (1),

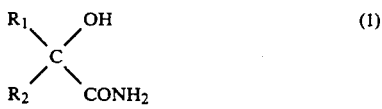
(1)

where $R_1$ and $R_2$ are independently selected from the group consisting of hydrogen and $C_1$-$C_4$ alkyl groups, provided that at least one of $R_1$ and $R_2$ is the alkyl group, with water in the presence of a solid acid catalyst containing a high surface area rare earth phosphate anhydride having the monoclinic system structure producible by heating a rare earth phosphate of the hexagonal system structure at 60°-200° C. in a solution of at least one compound selected from the group consisting of inorganic acids, inorganic acid salts and inorganic acid esters where the molar ratio of the inorganic acid component to the rare earth phosphate of the hexagonal system structure is 0.5-400.

DESCRIPTION OF THE PREFERRED EMBODIMENTS

Figure 1:
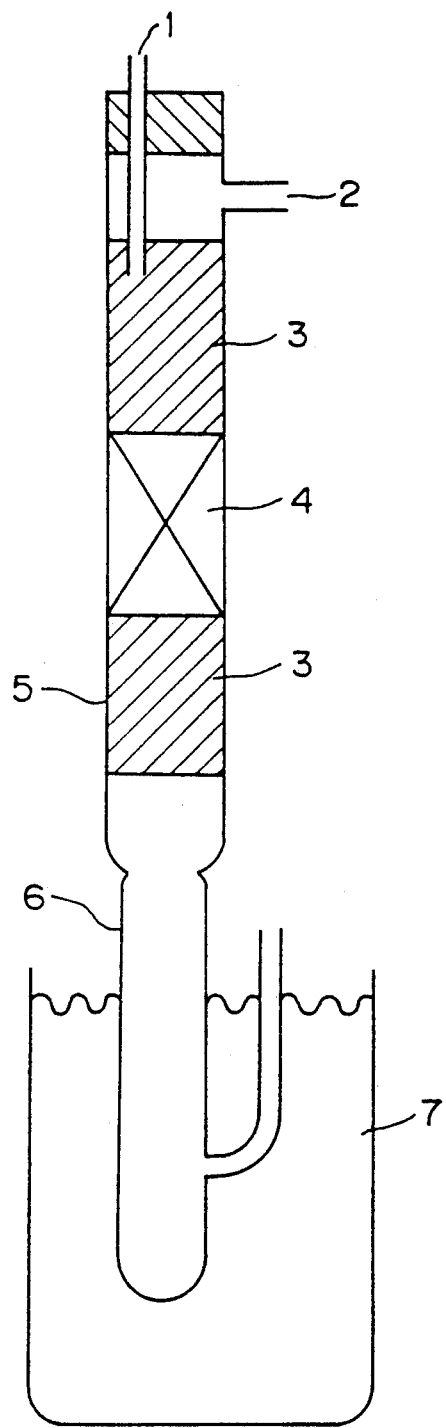
FIG. 1 shows schematically a cross sectional view of a reactor used in the examples of the present invention and comparative examples.

As a starting material for the process of the present invention, there is used an α-hydroxycarboxylic acid amide of the formula (1),

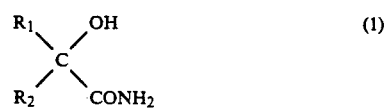
(1)

where $R_1$ and $R_2$ are independently selected from the group consisting of hydrogen and $C_1$-$C_4$ alkyl groups, provided that at least one of $R_1$ and $R_2$ is the alkyl group.

Exemplary suitable α-hydroxycarboxylic acid amides include:
lactamide,
α-hydroxybutyramide,
α-hydroxyisobutyramide,
α-hydroxyvaleramide,
α-hydroxyisovaleramide,
α-methyl-α-hydroxybutyramide, and the like.

These α-hydroxycarboxylic acid amides may be easily produced in high yield, for example, by hydrating cyanohydrins in the presence of a manganese dioxide catalyst as disclosed in U.S. Pat. No. 3,366,639.

The rare earth phosphate of the hexagonal system structure used in the present invention may be prepared by known methods, regardless of the state and concentration. However, the reaction in a solvent is preferable so as to obtain a high surface area phosphate.

For example, according to the method described in W. L. Jolly, Preparative Inorganic Reactions, Vol. 2, pages 139-167 (1965), Interscience Publishers, the preparation may be carried out as shown below.

An aqueous solution of a rare earth nitrate is mixed with phosphoric acid in an amount almost equimolar with said nitrate to cause a reaction and a slurry containing a precipitate is obtained. This slurry is aged directly or after neutralizing with aqueous ammonia. The resulting precipitate is washed with water by a decantation method or the like, and, directly or after filtration, dried or calcined to obtain a rare earth phosphate of the hexagonal system structure.

As the inorganic compounds in the solution used for heating the rare earth phosphate of the hexagonal system structure in the present invention, there may be used inorganic acids such as phosphoric acid, nitric acid, hydrochloric acid, sulfuric acid and the like; inorganic acid salts such as ammonium salt, sodium salt, potassium salt of such inorganic acid as above, or the like; and inorganic acid esters such as trimethyl phosphate, triethyl phosphate and the like.

The inorganic acid, inorganic acid salt and/or inorganic acid ester may be used as a solution in water or other solvent, preferably a solution in water.

According to the present invention, the molar ratio (HA/RPO$_4$) of the inorganic acid component in the solution of the inorganic acid, the inorganic acid salt and/or the inorganic acid ester used for heating the rare earth phosphate of the hexagonal system structure (HA) to the rare earth phosphate of the hexagonal system structure (RPO$_4$) is preferably 0.5–400.

When the ratio is less than 0.5, the heat treatment takes a long time. When the ratio exceeds 400, separation of the rare earth phosphate in the later treatment becomes difficult.

The solution temperature for the heat treatment is preferably 60°–200° C. At a temperature lower than 60° C., a long time is necessary for the heat treatment while at a temperature exceeding 200° C. the temperature of the solution becomes sometimes higher than the boiling point even at atmospheric pressure though this varies depending on the species of the solution and the concentration thereof and therefore, the handling becomes inconvenient.

The time necessary for the heat treatment is usually 0.2 hour or more though this varies depending on the temperature of the solution and the concentration of the solution. When the heating time is less than 0.2 hour, the heating treatment is insufficient so that the end product, the rare earth phosphate containing the monoclinic system structure, can not be obtained.

In the present invention, the "rare earth phosphate anhydride" is a phosphate containing at least one element selected from rare earth elements, containing no water of crystallization, and the crystal system containing a monoclinic system structure.

The solid acid catalyst containing a rare earth phosphate anhydride is the rare earth phosphate anhydride itself, or the rare earth phosphate anhydride mixed with or carried on a carrier such as oxides, sulfates, phosphates excluding rare earth phosphates and the like.

For example, the oxide is silica, the sulfate is aluminum sulfate, and the phosphate is magnesium phosphate, but these are not limitative.

The method for mixing or carrying may be that used in conventional catalyst preparations such as kneading, coprecipitation, soaking, chemical vapor deposition and the like.

The amounts of the starting materials used in the present invention are not particularly critical However, water is usually used in an amount not exceeding 200 moles, preferably 1–50 moles based on 1 mole of the α-hydroxycarboxylic acid amide.

The reaction method used in the present invention may be a vapor phase or a liquid phase method, and preferably a vapor phase method or a vapor and liquid mixed phase method, and the reaction may be conducted in an optional system such as, a fixed bed system, a fluidized bed system and the like.

According to the present invention, the reaction temperature is usually 150°–500° C., preferably 200–450° C. The reaction pressure may be usually atomospheric pressure. However, the reaction may be carried out at a pressure higher or lower than atmospheric pressure.

The feeding rate of a starting material, α-hydroxycarboxylic acid amide, may be widely varied depending on the kind of the catalyst, reaction temperature and the like. The feeding rate of 0.005–10 hr$^{-1}$ in terms of a liquid hourly space velocity (LHSV) is sufficient in usual.

In the reaction procedure, the starting material may be brought into contact with the catalyst layer together with an inert gas such as a nitrogen gas and the like.

Ammonia or aqueous ammonia may be fed to the catalyst layer as a pretreatment procedure before starting the reaction though such pretreatment is not always necessary.

According to the present invention, the α, β-unsaturated carboxylic acid can be produced in good yield from the α-hydroxycarboxylic acid amide. It is also possible to give a good yield under the conditions of a high catalytic load, a low reaction temperature, a long period of time and/or a continuous production.

In the following, the present invention is explained in detail referring to examples and comparative examples.

In all of these examples and comparative examples, there was used a reaction tube 5 having a catalyst layer 4 as illustrated in FIG. 1. In the following, "%" is by weight unless otherwise specified. Further, with respect to the prepared rare earth phosphates, the X-ray diffraction diagram was measured by means of an X-ray diffractometer (XD-D1, trade name, manufactured by Shimadzu Corporation), the specific surface area by means of a surface area measuring apparatus (Flowsorb II-2300, trade name, manufactured by Micromeritics Co.) and the thermal analysis by means of a thermal analysis apparatus (DTA - 50, TGA-50, trade name, manufactured by Shimadzu Corporation).

PREPARATION EXAMPLE

Lanthanum nitrate [La(NO$_3$)$_3$.6H$_2$O] 50.0 g (0.115 mole) was dissolved in water 200 ml. To the resulting solution was dropwise added a 85% phosphoric acid (H$_3$PO$_4$) 17.0 g (corresponding to 0.147 mole) diluted with 20 ml of water with stirring and a white precipitate formed. The resulting solution containing the white precipitate was heated to 60° C., aged for one hour with stirring, and then neutralized with 15% aqueous ammonia 54.2 g (corresponding to 0.478 mole).

After aging for 3 hours, the white precipitate was sufficiently washed with water by a decantation method, separated by filtration, washed with water, and dried at 120° C. for 24 hours to obtain lanthanum phosphate.

The X-ray diffraction diagram of this lanthanum phosphate was similar to lanthanum phosphate having the hexagonal system structure. Table 1 shows the relation of 2θ (θ:diffraction angle) of a powder X-ray diffraction diagram by means of CuKα X-ray of the lanthanum phosphate as obtained above and the relative intensity.

This relative intensity (%) is expressed by using the strongest diffraction ray (2θ=31.09°) as the standard. This value is not the absolute one since it varies depending on the degree of crystallization.

EXAMPLE 1

The lanthanum phosphate produced in Preparation Example as above 26.3 g (corresponding to 0.104 mole) was heated in a 50% phosphoric acid 106 g (corresponding to 0.54 mole) as an inorganic acid at a liquid temperature of 110° C. for 21 hours with stirring. The molar ratio of HA/RPO$_4$ was 5.2.

Then the resulting mixture was subjected to a sufficient decantation until the supernatant solution became neutral, separated by filtration and washed with water.

The resulting white precipitate was dried at 120° C. for 24 hours, calcined in air at 500° C. for 4 hours and shaped into particles of 10–16 mesh to prepare lanthanum phosphate anhydride containing the monoclinic system structure.

The resulting lanthanum phosphate anhydride had a specific surface area of 72.2 m$^2$/g and the X-ray diffraction diagram of powder thereof was similar to that of lanthanum phosphate having a monoclinic system structure.

Table 2 shows the relation between $2\theta$ ($\theta$:diffraction angle) of powder X-ray diffraction diagram by means of CuK$\alpha$ X-ray of the above-mentioned lanthanum phosphate and the relative intensity. The relative intensity (%) is expressed by using the strongest diffraction ray ($2\theta = 30.91°$) as the standard. This value is not the absolute one since it varies depending on the degree of crystallization.

The thermal analysis did not show a decrease in the weight due to release of water of crystallization and an endothermic phenomenon.

Now referring to FIG. 1, a catalyst layer 4 in a Pyrex glass reaction tube 5 of 12 mm in inner diameter was packed with 5 ml of the lanthanum phosphate anhydride (LaPO$_4$) catalyst prepared as above, and an evaporation part 3 with melted alumina balls of 3 mm in diameter.

Reaction tube 5 was fixed to an electric furnace capable of controlling the temperature of the catalyst layer 4 and connected with a reaction fluid receiver 6 cooled with a dry ice trap 7.

Then, nitrogen gas was fed to catalyst layer 4 at a rate of 10 ml/min (gas hourly space velocity (GHSV), 120 hr$^{-1}$) through a carrier gas feeding tube 2 at the upper part of reaction tube 5, and the temperature of catalyst layer 4 was set at 280° C.

Then a 9.0 mole % aqueous solution of $\alpha$-hydroxyisobutyramide (molar ratio of $\alpha$-hydroxyisobutyramide to water being 1:10) was fed through a starting material feeding tube 1 at a rate of 4.8 ml/hr (LHSV, 0.96 hr$^{-1}$).

A reaction fluid fraction during one hour between 1 hour and 2 hours after starting the feeding of the starting material and that between 240 and 241 hours after starting the feed of the starting material were captured in dry ice trap 7 and analyzed by gas chromatography. The yields of methacrylic acid (hereinafter called "MAA") based on the starting material, $\alpha$-hydroxyisobutyramide were 93.5 mole % and 92.4 mole %, respectively.

Table 3 shows the result.

EXAMPLE 2

The first half procedure of Example 1 was repeated except that a 70% phosphoric acid 1000 g (corresponding to 7.14 moles, HA/RPO$_4$=68.7) was used as an inorganic acid, and lanthanum phosphate anhydride containing the monoclinic system structure was obtained.

The resulting lanthanum phosphate anhydride had a specific surface area of 65.4 m$^2$/g and its powder X-ray diffraction diagram was similar to that of lanthanum phosphate having the monoclinic system structure.

As a result of the thermal analysis, there were not observed an endothermic phenomenon and a decrease in weight due to the release of water of crystallization. A reaction was carried out following the latter half procedure of Example 1 by using this lanthanum phosphate anhydride (LaPO$_4$) catalyst and MAA was produced.

The result is shown in Table 3.

EXAMPLE 3

The procedure of Preparation Example was repeated except that lanthanum nitrate was replaced with cerium nitrate, and cerium phosphate was obtained. The X-ray diffraction diagram of this product was similar to that of cerium phosphate having the hexagonal system structure.

The procedure of the first half of Example 1 was repeated except that lanthanum phosphhate was replaced with the cerium phosphate as obtained above, and there was obtained cerium phosphate anhydride containing the monoclinic system structure.

The cerium phosphate anhydride thus obtained had a specific surface area of 72.5 m$^2$/g and the X-ray diffraction diagram of the powder was similar to that of cerium phosphate having the monoclinic system structure.

As a result of the thermal analysis, there were not observed any decrease in the weight due to the release of water of crystallization and any endothermic phenomenon.

Further, 5 ml of the resulting cerium phosphate anhydride (CePO$_4$) catalyst was used to repeat the latter half procedure of Example 1 and MAA was obtained. Table 3 shows the result.

EXAMPLE 4

The procedure of Preparation Example was repeated except that lanthanum nitrate was replaced with neodymium nitrate, and neodymium phosphate was obtained. The X-ray diffraction diagram of this product was similar to that of neodymium phosphate having the hexagonal system structure.

The procedure of the first half of Example 1 was repeated except that lanthanum phosphate was replaced with the neodymium phosphate as obtained above, and there was obtained neodymium phosphate anhydride containing the monoclinic system structure.

The neodymium phosphate anhydride thus obtained had a specific surface area of 70.4 m$^2$/g and the X-ray diffraction diagram of the powder was similar to that of nedymium phosphate having the monoclinic system structure.

As a result of the thermal analysis, there were not observed any decrease in the weight due to the release of water of crystallization and any endothermic phenomenon.

Further, 5 ml of the resulting nedymium phosphate anhydride (NdPO$_4$) catalyst was used to repeat the latter half procedure of Example 1 and MAA was obtained. Table 3 shows the result.

EXAMPLE 5

The procedure of Preparation Example was repeated except that lanthanum nitrate was replaced with praseodymium nitrate, and praseodymium phosphate was obtained. The X-ray diffraction diagram of this product was similar to that of praseodymium phosphate having the hexagonal system structure.

The procedure of the first half of Example 1 was repeated except that lanthanum phosphate was replaced with the praseodymium phosphate as obtained above, and there was obtained praseodymium phosphate anhydride containing the monoclinic system structure.

The praseodymium phosphate anhydride thus obtained had a specific surface area of 65.4 m²/g and the X-ray diffraction diagram of the powder was similar to that of praseodymium phosphate having the monoclinic system structure.

As a result of the thermal analysis, there were not observed any decrease in the weight due to the release of water of crystallization and any endothermic phenomenon.

Further, 5 ml of the resulting praseodymium phosphate anhydride ($PrPO_4$) catalyst was used to repeat the latter half procedure of Example 1 and MAA was obtained. Table 3 shows the result.

EXAMPLE 6

The prodedure of Preparation Example was repeated except that lanthanum nitrate was replaced with a mixture of rare earth nitrates, and a mixture of rare earth phosphates was obtained.

The mixture of rare earth nitrates were prepared as shown below.

A commercially available mixture of rare earth oxides (purity of rare earth 98%: La 25%, Ce 51%, Nd 17%, Pr 5%) 19.0 g (corresponding to 0.058 mole) was dissolved in a 60% nitric acid 36.3 g (corresponding to 0.35 mole) at room temperature, and an aqueous solution of mixed rare earth nitrates was obtained.

The procedure of the first half of Example 1 was repeated except that lanthanum phosphate was replaced with the mixture of rare earth phosphates as obtained above, and there was obtained a mixture of rare earth phosphate anhydrides containing the monoclinic system structure.

The mixture of rare earth phosphate anhydrides had a specific surface area of 69.2 m²/g.

As a result of the thermal analysis, there were not observed any decrease in the weight due to the release of water of crystallization and any endothermic phenomenon.

Further, 5 ml of the resulting mixture of rare earth phosphate anhydrides was used to repeat the latter half of Example 1 and MAA was obtained. Table 3 shows the result.

EXAMPLES 7 AND 8

The procedure of Example 6 was repeated except that each commercially available mixture of rare earth oxides was used which was different from that of Example 6 in purity of rare earth and the components, and there was obtained a mixture of rare earth phosphate anhydrides containing the monoclinic system structure.

Further, 5 ml of the resulting mixture of rare earth phosphate anhydrides was used to repeat the procedure of the latter half of Example 1, and MAA was obtained.

Table 3 shows the result.

EXAMPLE 9

There were kneaded 1.05 g of the lanthanum phosphate anhydride obtained in the procedure of the first half of Example 1 and 20 g of silica (SILICA 951 W, trade name, manufactured by Fuji Davison Co.) subjected to a heat treatment at 1000° C. for 5 hours, and the mixture thus kneaded was calcined in air at 500° C. for 4 hours to obtain a silica carrying 5% of lanthanum phosphate.

Further, 5 ml of the silica carrying lanthanum phosphate was used to follow the procedure of the latter half of Example 1, and MAA was obtained.

The result is shown in Table 3.

COMPARATIVE EXAMPLE 1

Lanthanum phosphate obtained in Preparation Example 26.3 g (corresponding to 0.104 mole) was calcined in air at 800° C. for 4 hours, and shaped into particles of 10–16 mesh to produce a lanthanum phosphate anhydride having the monoclinic system structure.

The X-ray diffraction diagram of the powder highly consisted with that of lanthanum phosphate having the monoclinic system structure, and as a result of the thermal analysis, there were not observed an endothermic phenomenon and a decrease in weight attributable to release of water of crystallization. However, the specific surface area was as small as 12.1 m²/g.

Further, 5 ml of the resulting lanthanum phosphate anhydride ($LaPO_4$) catalyst was used to repeat the latter half procedure of Example 1, and MAA was obtained. The result is shown in Table 3.

COMPARATIVE EXAMPLE 2

The first half procedure of Example 1 was repeated except that the liquid temperature was 30° C. in place of 110° C., and lanthanum phosphate was obtained The resulting lanthanum phosphate had a specific surface area of 69.5 m²/g, but its powder X-ray diffraction diagram substantially consisted with that of lanthanum phosphate of the hexagonal system structure and did not have a feature of the monoclinic system structure.

As a result of thermal analysis, there were observed at about 220° C. a decrease in weight and an endothermic phenomenon attributable to release of water of crystallization.

Further, 5 ml of the resulting lanthanum phosphate catalyst was used to follow the procedure of the latter half of Example 1, and MAA was obtained.

Table 3 shows the result.

COMPARATIVE EXAMPLE 3

The procedure of the first half of Example 1 was repeated except that a 2% phosphoric acid 100 g (corresponding to 0.02 mole) was used as an inorganic acid and the molar ratio of $HA/RPO_4$ was 0.2, and lanthanum phosphate was obtained.

The resulting lanthanum phosphate had a specific surface area of 70.4 m²/g, but its powder X-ray diffraction diagram substantially consisted with that of lanthanum phosphate of the hexangonal system structure and did not have a feature of the monoclinic system structure.

As a result of thermal analysis, there were observed at about 220° C. a decrease in weight and an endothermic phenomenon attributable to release of water of crystallization.

Further, 5 ml of the resulting lanthanum phosphate catalyst was used to follow the procedure of the latter half of Example 1, and MAA was obtained. Table 3 shows the result.

EXAMPLES 10–18

The procedure of the first half of Example 1 was repeated except that the kind, concentration, amount and temperature of the solution for heating lanthanum phosphate were different from those in Example 1, and lanthanum phosphate anhydride containing the monoclinic system structure was obtained.

Table 4 shows the kind, concentration, temperature and HA/RPO$_4$. The amount of the solution was 100 g in each Example.

The powder X-ray diffraction diagram of the resulting lanthanum phosphate anhydride was similar to that of lanthanum phosphate having the monoclinic system structure.

As a result of the thermal analysis, there were not observed any decrease in the weight due to the release of water of crystallization and any endothermic phenomenon.

Then, 5 ml of the resulting lanthanum phosphate and hydride (LaPO$_4$) catalyst was used to follow the procedure of the latter half of Example 1, and MAA was obtained.

Table 4 shows the results.

EXAMPLES 19-21

The procedure of Example 1 was repeated except that the kinds of the reaction starting material, α-hydroxycarboxylic acid amide, and the reaction temperatures were different from those in Example 1.

Table 5 shows the results.

TABLE 1

| 2θ (°) | Relative Intensity (%) |
|---|---|
| 13.50 | 40 |
| 18.68 | 11 |
| 20.11 | 25 |
| 20.78 | 17 |
| 25.15 | 28 |
| 26.99 | 17 |
| 28.74 | 87 |
| 31.09 | 100 |
| 37.32 | 17 |
| 41.37 | 52 |
| 45.75 | 14 |
| 46.42 | 25 |
| 48.08 | 51 |
| 50.35 | 12 |
| 51.51 | 25 |
| 53.69 | 16 |
| 58.81 | 12 |

TABLE 2

| 2θ (°) | Relative Intensity (%) |
|---|---|
| 18.78 | 11 |
| 21.07 | 24 |
| 21.41 | 11 |
| 25.15 | 21 |
| 26.72 | 43 |
| 28.51 | 77 |
| 29.51 | 18 |
| 30.91 | 100 |
| 34.15 | 20 |
| 36.55 | 21 |
| 40.85 | 21 |
| 41.76 | 51 |
| 45.66 | 37 |
| 46.38 | 11 |
| 47.39 | 19 |
| 48.12 | 40 |
| 50.24 | 14 |
| 51.41 | 24 |
| 52.19 | 21 |
| 53.59 | 12 |
| 56.78 | 10 |
| 58.23 | 10 |
| 59.96 | 12 |
| 69.46 | 15 |

TABLE 3

| | Solution | | Catalyst | | MAA Yield (mole %) | | Productivity of Catalyst (*4) |
|---|---|---|---|---|---|---|---|
| | Temperature (°C.) | Molar Ratio HA/RPO$_4$ | Rare Earth Phosphate | Specific Surface Area (m$^2$/g) | 1-2 hrs. | 240-241 hrs. | |
| Example 1 | 110 | 5.2 | LaPO$_4$ | 72.2 | 93.5 | 92.4 | 64.3 |
| Example 2 | 110 | 68.7 | LaPO$_4$ | 65.4 | 92.1 | 90.6 | 63.3 |
| Example 3 | 110 | 5.3 | CePO$_4$ | 72.5 | 94.0 | 93.1 | 65.0 |
| Example 4 | 110 | 5.2 | NdPO$_4$ | 70.4 | 92.9 | 90.7 | 63.3 |
| Example 5 | 110 | 5.2 | PrPO$_4$ | 65.4 | 90.4 | 88.3 | 61.5 |
| Example 6 | 110 | 5.2 | Mixture (*1) | 69.2 | 90.1 | 88.4 | 61.7 |
| Example 7 | 110 | 5.2 | Mixture (*2) | 64.6 | 87.3 | 85.9 | 60.2 |
| Example 8 | 110 | 5.2 | Mixture (*3) | 65.7 | 88.5 | 86.6 | 60.5 |
| Example 9 | 110 | 5.2 | 5% LaPO$_4$/95% SiO$_2$ | 157.2 | 86.3 | 82.8 | 57.7 |
| Comparative Example 1 | — | — | LaPO$_4$ | 12.1 | 58.2 | 21.3 | 20.9 |
| Comparative Example 2 | 30 | 5.2 | LaPO$_4$.H$_2$O | 69.5 | 69.6 | 27.7 | 24.3 |
| Comparative Example 3 | 110 | 0.2 | LaPO$_4$.H$_2$O | 70.4 | 70.2 | 30.1 | 27.3 |

(*1) Purity of Rare Earth 98%: La 25%, Ce 51%, Nd 17%, Pr 5%
(*2) Purity of Rare Earth 99%: La 54%, Nd 34%, Pr 11%
(*3) Purity of Rare Earth 97%: La 18%, Nd 61%, Pr 18%
(*4) "Productivity of Catalyst" is the total weight of the produced MAA per unit weight of the catalyst (g/g-catalyst) after 241 hours from the beginning of feeding the starting material.

TABLE 4

| | Solution | | | Specific Surface Area of Catalyst (m$^2$/g) | Yield of MAA (mole %) |
|---|---|---|---|---|---|
| | Inorganic acid, or Salt or Ester thereof | Temperature (°C.) | Molar Ratio HA/RPO$_4$ | | |
| Example 10 | 60% HNO$_3$ | 120 | 9.2 | 67.2 | 89.5 |
| Example 11 | 20% HCl | 110 | 5.3 | 66.9 | 87.2 |
| Example 12 | 50% H$_2$SO$_4$ | 135 | 4.9 | 60.2 | 85.5 |
| Example 13 | 40% H$_3$PO$_4$ + 10% HNO$_3$ | 110 | 5.5 | 68.5 | 91.8 |
| Example 14 | 25% aqueous solu- | 100 | 2.0 | 68.5 | 88.3 |

TABLE 4-continued

| | Solution | | | Specific Surface | Yield of |
|---|---|---|---|---|---|
| | Inorganic acid, or Salt or Ester thereof | Temperature (°C.) | Molar Ratio HA/RPO$_4$ | Area of Catalyst (m$^2$/g) | MAA (mole %) |
| Example 15 | 20% aqueous solution of NaH$_2$PO$_4$ tion of KCl | 100 | 2.6 | 62.1 | 84.6 |
| Example 16 | 30% aqueous solution of NaNO$_3$ | 100 | 3.4 | 65.0 | 86.1 |
| Example 17 | 20% aqueous solution of NaHSO$_4$ | 100 | 1.6 | 60.7 | 82.8 |
| Example 18 | 30% aqueous solution of (CH$_3$O)$_3$PO | 135 | 2.1 | 63.5 | 86.7 |

TABLE 5

| | Starting Material | Reaction Temperature (°C.) | LHSV (hr$^{-1}$) | Product Compound | Yield (mole %) |
|---|---|---|---|---|---|
| Example 1 | α-Hydroxyisobutyramide | 280 | 0.96 | Methacrylic acid | 93.5 |
| Example 19 | α-Hydroxybutyramide | 290 | 0.96 | β-Methylacrylic acid | 87.4 |
| Example 20 | α-Hyddroxyisovaleramide | 280 | 0.96 | β,β-Diemthylacrylic acid | 84.2 |
| Example 21 | α-Methyl-α-hydroxybutyramide | 300 | 0.96 | β-Methylmethacrylic acid | 71.3 |

What is claimed is:

1. A process for producing an α,β-unsaturated carboxylic acid which comprises catalytically reacting an α-hydroxycarboxylic acid amide of the formula (1),

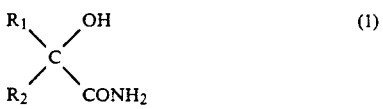

where R$_1$ and R$_2$ are independently selected from the group consisting of hydrogen and C$_1$-C$_4$ alkyl groups, provided that at least one of R$_1$ and R$_2$ is the alkyl group, with water in the presence of a solid acid catalyst containing a high surface area rare earth phosphate anhydride having the monoclinic system structure producible by heating a rare earth phosphate of the hexagonal system structure at 60°-200° C. in a solution of at least one compound selected from the group consisting of inorganic acids, inorganic acid salts and inorganic acid esters where the molar ratio of the inorganic acid component to the rare earth phosphate of the hexagonal system structure is 0.5-400.

2. The process according to claim 1 in which the rare earth phosphate of the hexagonal system structure is lanthanum phosphate.

3. The process according to claim 1 in which the rare earth phosphate of the hexagonal system structure is cerium phosphate.

4. The process according to claim 1 in which the rare earth phosphate of the hexagonal system structure is neodymium phosphate.

5. The process according to claim 1 in which the rare earth phosphate of the hexagonal system structure is praseodymium phosphate.

6. The process according to claim 1 in which the rare earth phosphate of the hexagonal system structure is composed of at least two phosphates selected from the group consisting of lanthanum, cerium, neodymium and praseodymium phosphates.

7. The process according to claim 1 in which the rare earth phosphate of the hexagonal system structure is at least one member selected from the group consisting of lanthanum and lanthanoid phosphates.

8. The process according to claim 1 in which the inorganic acid contains at least one member selected from the group consiting of phosphoric acid, nitric acid, hydrochloric acid and sulfuric acid.

9. The process according to claim 1 in which the inorganic acid is phosphoric acid.

10. The process according to claim 1 in which the inorganic acid is nitric acid.

11. The process according to claim 1 in which the inorganic acid is hydrochloric acid.

12. The process according to claim 1 in which the inorganic acid is sulfuric acid.

13. The process according to claim 1 in which the inorganic acid is a mixed acid of phosphoric acid and nitric acid.

14. The process according to claim 1 in which the inorganic acid is a mixed acid composed of at least two acids selected from the group consisting of phosphoric acid, nitric acid, hydrochloric acid and sulfuric acid.

15. The process according to claim 1 in which the inorganic acid salt solution contains at least one member selected from the group consisting of phosphate solutions, nitrate solutions, chloride solutions and sulfate solutions.

16. The process according to claim 1 in which the inorganic acid salt solution is a phosphate solution.

17. The process according to claim 1 in which the inorganic acid salt solution is a nitrate solution.

18. The process according to claim 1 in which the inorganic acid salt solution is a chloride solution.

19. The process according to claim 1 in which the inorganic acid salt solution is a sulfate solution.

20. The process according to claim 1 in which the inorganic acid salt solution is a mixture of a phosphate solution and a nitrate solution.

21. The process according to claim 1 in which the inorganic acid ester solution is a phosphoric acid ester solution.

22. The process according to claim 1 in which the α-hydroxycarboxylic acid amide is α-hydroxyisobutyramide.

* * * * *